(12) United States Patent
Khan

(10) Patent No.: US 6,384,253 B1
(45) Date of Patent: May 7, 2002

(54) COMPOSITE MATERIALS

(75) Inventor: M. Ishaque Khan, Skokie, IL (US)

(73) Assignee: Illinois Institute of Technology, Chicago, IL (US)

(*) Notice: Subject to any disclaimer, the term of this patent is extended or adjusted under 35 U.S.C. 154(b) by 0 days.

(21) Appl. No.: 09/677,721

(22) Filed: Oct. 2, 2000

Related U.S. Application Data

(60) Provisional application No. 60/156,986, filed on Oct. 1, 1999.

(51) Int. Cl.[7] .................................................. C07F 9/00
(52) U.S. Cl. ......................................... 556/44; 502/170
(58) Field of Search ............................. 556/44; 502/170

(56) References Cited

U.S. PATENT DOCUMENTS

| | | | |
|---|---|---|---|
| 3,076,830 A | 2/1963 | Conn | 260/429 |
| 4,745,203 A | 5/1988 | Nachbur | 556/4 |
| 4,965,381 A | 10/1990 | Kerby et al. | 556/18 |
| 5,364,952 A | 11/1994 | Spiess et al. | 556/44 |
| 5,648,508 A | 7/1997 | Yaghi | 556/9 |
| 5,659,034 A | 8/1997 | DeBord et al. | 346/2 |
| 5,888,993 A | 3/1999 | McNeil et al. | 514/186 |
| 5,914,417 A | 6/1999 | Reichert et al. | 556/42 |

Primary Examiner—Porfirio Nazario-Gonzalez
(74) Attorney, Agent, or Firm—Pauley Petersen Kinne & Erickson

(57) ABSTRACT

Composite materials composed of organic and inorganic substances of the general formulation $MO(O_2C—C_6H_4—CO_2)$, wherein M is a transition metal, and a method for producing the composite materials. The structure of these materials includes at least one column of an array of transition metal oxides, the column having corner-sharing octahedra interlinked with spacer organic chelating ligands. The inorganic-organic hybrid materials are likely to exhibit properties not encountered in pure inorganic and organic substances.

19 Claims, 2 Drawing Sheets

COMPOSITE MATERIALS

CROSS REFERENCE TO RELATED APPLICATION

This application claims the benefit of U.S. Provisional Application No. 60/156,986, filed Oct. 01, 1999.

BACKGROUND OF THE INVENTION

1. Field of the Invention

This invention relates to a composition of matter, namely composite materials including organic and inorganic components and having a general formulation [$MO(O_2C-C_6H_4-CO_2)$], wherein M is a transition metal.

2. Description of Prior Art

Composite materials comprising organic and inorganic substances are known in the art. Similarly, organo-metallic composites having a well-defined framework are also known. For example, U.S. Patent 4,965,381 teaches an organo-metallic polymer useful as a metathesis catalyst formed by reacting a carboxylate salt such as dimolybdenum tetra acetate with either tetra methyl ethylene diamine or dimethyl phosphino ethane and crystallizing the polymer. U.S. Patent 5,648,508 teaches a method for preparation of metal-organic crystalline or microcrystalline microporous materials in which a metal or metalloid ion is reacted under mild reaction conditions in solution with a ligand containing multidentate functional groups in the presence of a templating agent. The resulting microporous materials are indicated to be useful in the purification of liquids and gases. U.S. Patent 5,659,034 teaches vanadium oxide crystalline compositions having the general formula $(M_1)_a(M_2)_b(M_3)_c$ [$V_xO_y$]$_zH_2O$ in which the layered mixed-valence vanadium oxide forms host layers between which are intercalated either cationic transition or post-transition metal coordination complexes, monomeric ammonium or diammonium cations, or a mixture of alkali metal cations and monomeric ammonium or diammonium cations and where $M_1$ is a metal-coordination complex [$L_nA$]$^{+w}$, where L is a bidentate amine ligand, A is a transition or post-transition metal, n is equal to 1,2 or 3, and w is equal to 1,2,3, or 4. U.S. Patent 5,888,993 teaches vanadium compositions for use in the treatment of hypertension, obesity and diabetes, in particular, improved oral compositions comprising oxovanadium (IV) chelates of monoprotic, bidentate oxygen, oxygen and oxygen, nitrogen coordinating ligands, especially kojic acid, maltol and ethyl maltol.

U.S. Patent 5,914,417 teaches an organometallic compound of the general formula $M(OH)_x(A)_y(B)_z$, where M means Ti(IV), Nb(V) and Ta(V) and x+y+z=5 for Nb and Ta and x+y+z=4 for Ti and A means an alkoxide ligand of diols and/or glycol monoethers and B means a carboxylate ligand of fatty acids of a carbon chain length of $C_6$–$C_{19}$.

There is thus a need or desire for new composite materials.

More particularly, there is a need or desire for composite materials including organic and inorganic components, also including a transition metal, and having a perfect framework structure, thereby resulting in improved properties compared to pure organic and inorganic substances.

SUMMARY OF THE INVENTION

The present invention is directed to the combination of organic compounds with inorganic substances to prepare novel materials having the general formulation [$MO(O_2C-C_6H_4-CO_2)$], wherein M is a transition metal, with improved properties compared to pure inorganic and organic substances. Such composites are needed in many critical technology areas including nonlinear optics, optical switches, use as efficient catalysts, and magnetic and chemical sensing devices.

In the design and creation of these materials, two highly desirable types of components are combined, one each from organic and inorganic compounds. The materials are created by combining metal oxide based solids with desirable organics in such a way as to form at least one column of an array of transition metal oxides, with the column including corner-sharing octahedra interlinked with spacer organic chelating ligands, thereby forming a perfect framework structure having large tunnels.

In view of the perfect framework structure and large tunnels present in these compositions, these compositions may exhibit shape selective catalysis, selective oxidation of hydrocarbons performed in the petrochemical industry, molecular sieve action for separating individual components from a mixture, and may be used for chemical sensing of toxic and hazardous gases and explosives.

In view of the magnetic columns separated by dimagnetic organics in these compositions, these compositions may find application in electronic, magnetic, and optical devices.

The foregoing and other features and advantages of the present invention will become further apparent from the following detailed description of the presently preferred embodiments, read in conjunction with the accompanying drawings. The detailed description and drawings are intended to illustrate the present invention rather than limit the scope of the present invention as defined by the appended claims and equivalents of the appended claims.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

The composite materials of this invention are composed of organic and inorganic substances of a general formulation [$MO(O_2C-C_6H_4-CO_2)$], wherein M is a transition metal. By combining organic compounds and their functionalities with inorganic substances, the resulting compositions are likely to exhibit properties not encountered in pure inorganic and organic substances.

In producing these composite materials, the organic component and the inorganic component are combined to form at least one column, preferably two or more columns, of an array of transition metal oxides, with the columns having corner-sharing octahedra interlinked with robust spacer organic chelating ligands. These columns, aligned as described, create a perfect framework structure.

Figure 1:
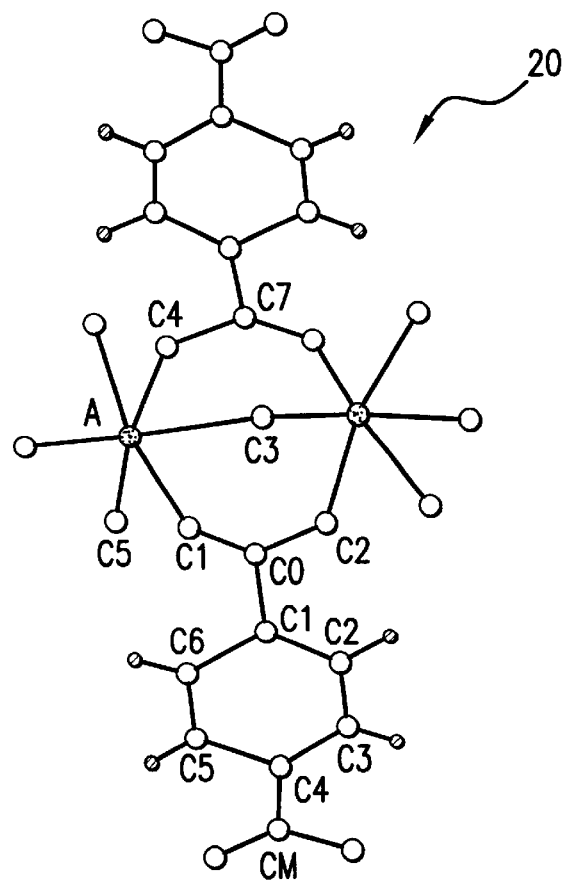
FIG. 1 shows the building block unit of a preferred embodiment of the invention.
Figure 2:
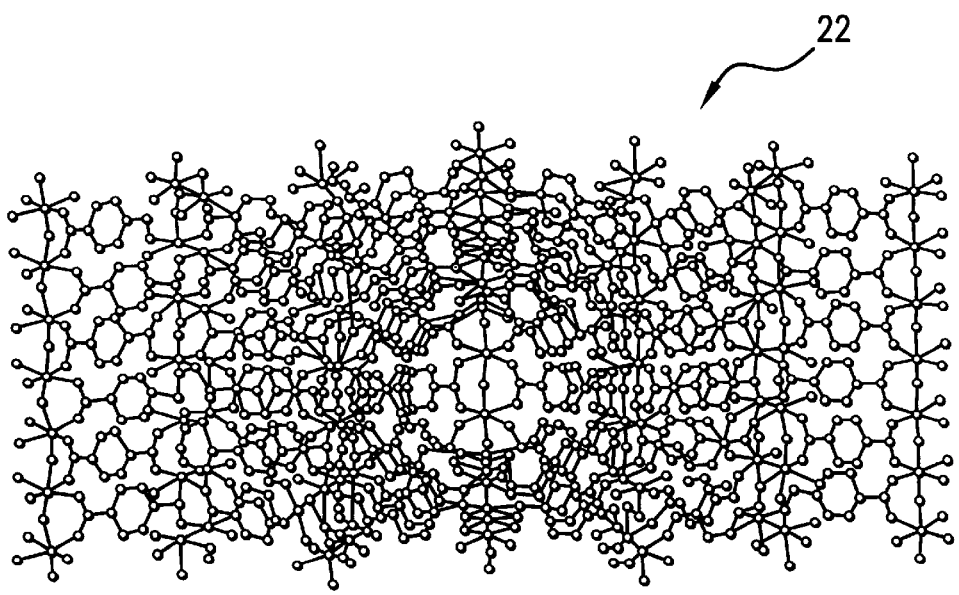
FIG. 2 is an x-ray crystal structure showing the extended structure of a preferred embodiment of the invention.
Figure 3:
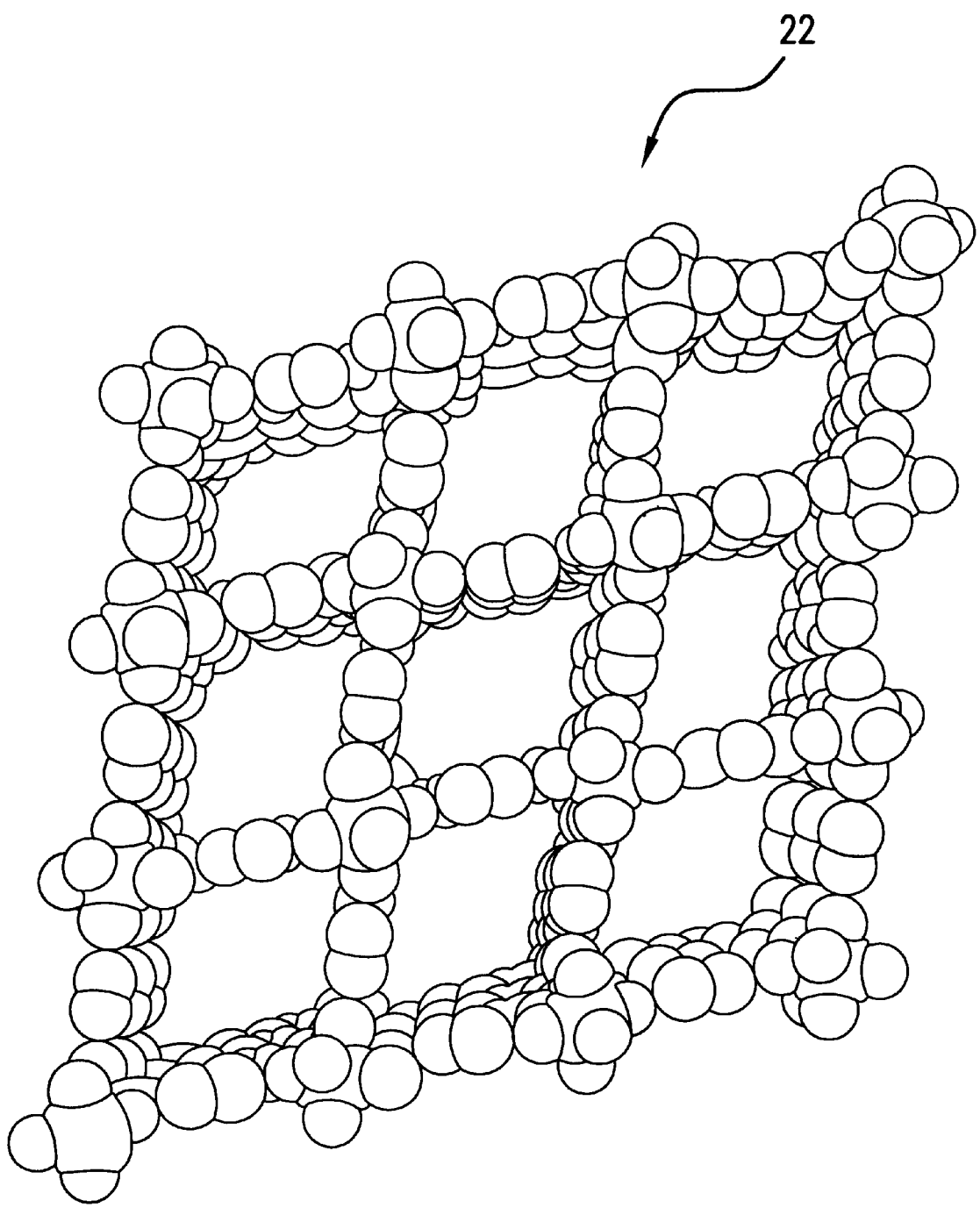
FIG. 3 is an x-ray crystal structure showing the 6×6 net framework structure of a preferred embodiment of the invention, and showing large tunnels generated within this structure.

All transition metals are suitable for use in this invention, with preferred transition metals including vanadium, niobium, and tantalum. FIG. 1 shows a building block unit 20 of the composite material of the invention using vanadium, namely a building block unit of [VO(O$_2$C—C$_6$H$_4$—CO$_2$)]. FIG. 2 is an x-ray crystal structure 22 of [VO(O$_2$C—C$_6$H$_4$—CO$_2$)] showing the extended structure of the composite material. More particularly, FIG. 3 shows the 6×6 net framework structure of the x-ray crystal structure 22 of [VO(O$_2$C—C$_6$H$_4$—CO$_2$)], clearly illustrating large tunnels generated within this structure.

The perfect framework structure and large tunnels present in the compositions of the invention are believed to cause the compositions to exhibit selective catalysis, selective oxidation of hydrocarbons performed in the petrochemical industry, molecular sieve action for separating individual components from a mixture, and are believed to render the compositions suitable, and highly desirable, for use in chemical sensing of toxic and hazardous gases and explosives. Furthermore, the magnetic columns in the perfect framework structure, separated by dimagnetic organics in the structure, are believed to render the compositions suitable, and highly desirable, for use in electronic, magnetic, and optical devices.

The composite materials of the invention can be made by mixing an inorganic sulfate having the formula MOSO$_4$.nH$_2$O with 1,4-benzenedicarboxylic acid and a dilute solution of sodium hydroxide. The mixture should be heated for between about 50 and 100 hours, suitably for between about 20 and 90 hours, at a temperature between about 150° and 250° Celsius, suitably between about 175° and 225° Celsius. After heating the mixture, the mixture is then cooled at room temperature. Suitably, the mixture is allowed to cool for between about 2 and 10 hours, more suitably for between about 3 and 7 hours. Once the mixture is cooled, any solids formed in the mixture are filtered from any liquid in the mixture. The filtered solids are then washed with cold water and allowed to dry. The filtered solids can be dried in air at room temperature. Furthermore, a small amount of impurity can be readily removed from the filtered solids by washing the filtered solids with a slightly alkaline solution, such as triethylamine, to obtain pure composite material in high yield. A more specific example of producing [VO(O$_2$C—C$_6$H$_4$—CO$_2$)], in particular, is described below.

EXAMPLE

In this example, [VO(O$_2$C—C$_6$H$_4$—CO$_2$)] was produced in accordance with the invention. The reaction was carried out in a 23 mL Parr™ Teflon™-lined acid digestion bomb, heated in a Thermolyne™ programmable electric furnace. A mixture of vanadylsulfate-VOSO$_4$.nH$_2$O, 1,4-benzenedicarboxylic acid, and a dilute (0.5 M) solution of sodium hydroxide in the molar ratio 3:3:2.5 was placed in the 23 mL Parr™ Teflon™-lined autoclave which was subsequently heated for 70 hours inside an electric furnace maintained at 200° Celsius. After cooling the autoclave at room temperature for 4 hours, orange-brown needles were filtered from a blue mother liquor. The orange-brown needles were then washed with cold water and dried in air at room temperature. A small amount of impurity was readily removed by washing the orange-brown needles with triethylamine to obtain pure composite material in high yield.

Selected IR bands of the resulting composition, [VO(O$_2$C—C$_6$H$_4$—CO$_2$)], using a KBr pellet; 2000–400 cm$^{-1}$ region: 1729(m), 1700(s), 1690(s), 1611(w), 1575(m), 1539(s), 1503(m), 1459(m), 1421(s), 1415(m), 1395(s), 1317(m), 1280(s), 1244(m), 1133(w), 1104(w), 1018(m), 989(w), 897(s), 877(m), 824(w), 772(m), 736(s), 727(s), 605(m), 572(s). Crystal data for the composition was as follows: Orthorhombic, space group P2$_1$ 2$_1$ 2$_1$, a=12.4477, b=17.1501, c=6.8020 Å.

While in the foregoing specification this invention has been described in relation to certain preferred embodiments thereof, and many details have been set forth for purpose of illustration, it will become apparent to those skilled in the art that the invention is susceptible to additional embodiments and that certain of the details described herein can be varied considerably without departing from the basic principles of the invention.

What is claimed is:

1. A composition having the formula MO(O$_2$C—C$_6$H$_4$—CO$_2$), wherein M is a transition metal.

2. The composition of claim 1, wherein M is vanadium.

3. The composition of claim 1, wherein M is niobium.

4. The composition of claim 1, wherein M is tantalum.

5. A composition comprising organic and inorganic components, and having the formula MO(O$_2$C—C$_6$H$_4$—CO$_2$), wherein M is a transition metal.

6. The composition of claim 5, wherein M is vanadium.

7. The composition of claim 5, wherein M is niobium.

8. The composition of claim 5, wherein M is tantalum.

9. A composition comprising:

at least one column of an array of transition metal oxides, the at least one column including corner-sharing octahedra interlinked with spacer organic chelating ligands.

10. The composition of claim 9, wherein the composition has the formula MO(O$_2$C—C$_6$H$_4$—CO$_2$), wherein M is a transition metal.

11. A method for producing a composition having the formula MO(O$_2$C—C$_6$H$_4$—CO$_2$), wherein M is a transition metal, the method comprising the steps of:

mixing an inorganic sulfate having the formula MOSO$_4$.nH$_2$O with 1,4-benzenedicarboxylic acid and a dilute solution of sodium hydroxide;

heating the mixture for about 70 hours at a temperature of about 200° Celsius, forming a heated mixture;

cooling the heated mixture at room temperature, forming solids in the mixture;

filtering the solids from the mixture;

washing the solids with cold water; and drying the solids.

12. A method in accordance with claim 11, wherein the dried solids are washed with an alkaline solution resulting in removal of any impurities in the solids.

13. The method of claim 12, wherein the alkaline solution comprises triethylamine.

14. The method of claim 11, wherein M is vanadium.

15. The method of claim 11, wherein M is niobium.

16. The method of claim 11, wherein M is tantalum.

17. The method of claim 11, wherein the inorganic sulfate, 1,4-benzenedicarboxylic acid, and sodium hydroxide are mixed in a molar ratio of 3:3:2.5.

18. The method of claim 11, wherein the dilute solution of sodium hydroxide is a 0.5 M solution.

19. The method of claim 11, wherein the mixture is cooled for about 4 hours.

* * * * *